United States Patent [19]

Nugent et al.

[11] 4,398,544
[45] Aug. 16, 1983

[54] SINGLE AND MULTIPLE SAMPLE NEEDLE ASSEMBLY WITH VEIN ENTRY INDICATOR

[75] Inventors: Edward L. Nugent, North Caldwell; Joseph Kaufman, Emerson, both of N.J.

[73] Assignee: Becton Dickinson and Company, Paramus, N.J.

[21] Appl. No.: 311,494

[22] Filed: Oct. 15, 1981

[51] Int. Cl.$^3$ ................................................. A61B 5/14
[52] U.S. Cl. .................................... 128/763; 128/766; 604/236; 604/240
[58] Field of Search ......................... 128/760, 762–766, 128/214.4, 218 NV, 274; 73/863.51, 863.54; 604/236, 240, 247, 249, 256

[56] References Cited

U.S. PATENT DOCUMENTS

| | | | |
|---|---|---|---|
| 3,659,587 | 5/1972 | Baldwin | 128/218 NV X |
| 3,874,367 | 4/1975 | Ayres | 128/218 NV X |
| 3,886,930 | 6/1975 | Ryan | 128/764 |
| 4,133,304 | 1/1979 | Bailey | 128/764 |
| 4,160,383 | 7/1979 | Rauschenberger | 128/274 X |
| 4,192,919 | 3/1980 | Raghavachari | 128/764 X |
| 4,207,870 | 7/1980 | Eldridge | 128/764 X |
| 4,244,378 | 1/1981 | Brignola | 128/764 X |
| 4,307,731 | 12/1981 | Kaufman | 128/764 X |
| 4,340,068 | 7/1982 | Kaufman | 128/218 NV X |

Primary Examiner—Lee S. Cohen
Assistant Examiner—Angela D. Sykes

[57] ABSTRACT

A single or multiple liquid sample needle assembly is provided. The assembly includes a housing with a receiving chamber having translucent or transparent walls for determining whether access to the sample in question has been achieved. The invention utilizes a porous plug in the chamber which provides, simultaneously, a liquid barrier for the sample received, and gas displacement venting means for gas displaced by the liquid sample received. The assembly may be modified to receive only a single sample for subsequent discharge to a vacuum collection device, or multiple samples for sequential discharge to a plurality of vacuum collection devices. For multiple collection, the assembly incorporates a flexible sleeve and a separate gas discharge opening in combination with the sample discharge opening of the assembly.

10 Claims, 9 Drawing Figures

SINGLE AND MULTIPLE SAMPLE NEEDLE ASSEMBLY WITH VEIN ENTRY INDICATOR

BACKGROUND AND STATEMENT OF THE INVENTION

This invention relates to an assembly for collecting a liquid sample from a patient, such as a blood sample. More particularly, this invention relates to a needle assembly for collecting either a single or a multiple liquid sample from such a patient. The device of the invention utilizes a receiving chamber with walls which are translucent or transparent for visually indicating whether or not proper access to the sample in question has been achieved. Moreover, the chamber incorporates therein a reciprocal porous plug which plug is comprised of material which provides simultaneously a liquid barrier for the sample received, and a gas displacement discharge passage for gas displaced by the liquid sample received in the chamber.

The plug reciprocates in the chamber as required to first receive the liquid sample in question, while sealing the chamber against discharge of the sample, and simultaneously venting gas displaced by the liquid sample. Subsequently, when the liquid sample is to be discharged to either a single vacuum collection device or a plurality of them, the plug reciprocates to cooperate with certain vents in the discharge area of the assembly for allowing passage of the collected sample to discharge sequentially to one or more vacuum collection devices. In those instances where multiple samples are to be collected and sequentially discharged to a plurality of vacuum collection devices, the assembly incorporates a flexible sleeve which cooperates with the discharge opening of the device during periods of exchange of the vacuum collection devices for a subsequent discharge of an additional sample.

As discussed above, it is desirable to provide a mechanism whereby the user of such a needle assembly can be informed when the intravenous needle has penetrated the vein of the patient for collection of a blood sample. Many times in collecting blood from a patient it is difficult to locate the vein, or for other reasons blood flow into the collecting device is not adequate. In those instances, it is advantageous to be able to make a quick determination that entry into the vein has been made and that blood is flowing into the needle assembly. Once this determination has been made and the vein entry achieved, the evacuated blood collection container can be inserted into the collection assembly in accordance with well known techniques of collecting blood samples during a single collection procedure.

One of the problems which arise during the venipuncture step concerns the pockets of air which are found in various needle assemblies for either single or multiple sample blood collections. When venipuncture is made, and the evacuated blood collection container is not yet attached to the opposite end of the needle structure, blood cannot always flow into the needle assembly because of a pocket of air which, under normal atmospheric conditions, remains inside the needle assembly. Thus, even though vein entry may have been accomplished, blood flow may not have begun, simply because of the air pocket blockage in the assembly.

With this invention, by contrast, through the utilization of a porous vent plug in the collection chamber, the plug allows for displacement of the air from the collection chamber so as to allow room for receiving the blood sample being collected. Moreover, the plug is so arranged to be reciprocable in the chamber to cooperate with vents in a discharge negative pressure cannula in the assembly for first venting the displaced air during the receiving portion of the procedure for receiving the sample, and subsequently discharging the sample to the vacuum blood collection container when such a container is attached to the assembly. For example, in one embodiment of the invention, for a single sample collection procedure, the assembly of the invention includes a porous plug which vents the displaced air when the sample is received, and then moves in response to a pressure differential to open passages in the assembly to discharge the sample received into an evacuated blood collection container, when such container is attached to the assembly and the discharge negative pressure cannula penetrates into the vacuum of an evacuated collection container.

Another embodiment of the invention includes a flexible sleeve covering the discharge opening of the negative pressure cannula. The flexible sleeve is so arranged to allow discharge from a third air discharge vent in the discharge cannula during the sample receiving procedure. Subsequently, the flexible sleeve is flexed and moved to cover this discharge opening when an evacuated blood collection container is inserted into the assembly for penetration by the negative pressure cannula. Once a single sample has been obtained in the evacuated blood collection container, and the container removed from the assembly, the flexible sleeve again covers the discharge opening in the negative pressure cannula until such time as subsequently, an additional evacuated blood collection container is attached for a subsequent collection of a second sample. As will be obvious to practitioners-in-the-art, this procedure may be repeated for collecting the number of samples required in individual evacuated blood collection containers.

In considering the utilization of a porous plug in blood collection assemblies of the kind described herein, in a previously filed patent application entitled "Blood Sampling Assembly Having Vein Entry Indicator" by William N. Eldridge, U.S. Ser. No. 915,670 filed June 15, 1978, now U.S. Pat. No. 4,207,870 issued June 17, 1980 and assigned to the common assignee herewith, the inventor recognized that this air blockage problem prevented the blood from flowing as desired through the intravenous needle to a point where it could be seen by a user. In the Eldridge invention, a porous vent means is provided in combination with a one-way valve whereby air inside the needle assembly is allowed to pass out of this venting means during the initial stages of the blood collection procedure. The venting means prevents the passage of blood until the user attaches the evacuated blood collection container to the needle assembly. Once the negative pressure of the evacuated blood collection container is attached, a separate one-way valve opens and allows blood to travel from the vein of the patient, and through the needle assembly and on into the container.

Although the Eldridge invention recognizes the utilization of a porous material for providing a venting for displaced air during receiving a blood sample, there is still room for improvement over such a device and particularly with respect to the present invention wherein the plug is a reciprocal plug which operates not only as a vent, but also as a valve structure in and of itself with no separate complicated structure for use in providing the valving action. Thus, the plug of the invention herein sealingly engages in reciprocal cooperation with the blood receiving chamber for simultaneously blocking discharge of the blood sample while venting displaced air from the receiving chamber and subsequently reciprocating to allow discharge of the received sample at the moment when the assembly is attached to an evacuated blood collection container.

Other related applications include U.S. patent application Ser. No. 160,781 filed June 18, 1980, now U.S. Pat. No. 4,340,068 issued July 20, 1982 and co-pending U.S. patent application Ser. No. 284,894, filed July 20, 1981 entitled "Multiple Sample Needle Assembly With Vein Entry Indicator".

Other objects and advantages of this invention will be apparent from the following description, the accompanying drawings and the appended claims.

DETAILED DESCRIPTION OF THE DRAWINGS

FIG. 6 is a cross-sectional view taken along lines 6—6 of FIG. 4;

DETAILED DESCRIPTION OF THE DRAWINGS

Figure 1:
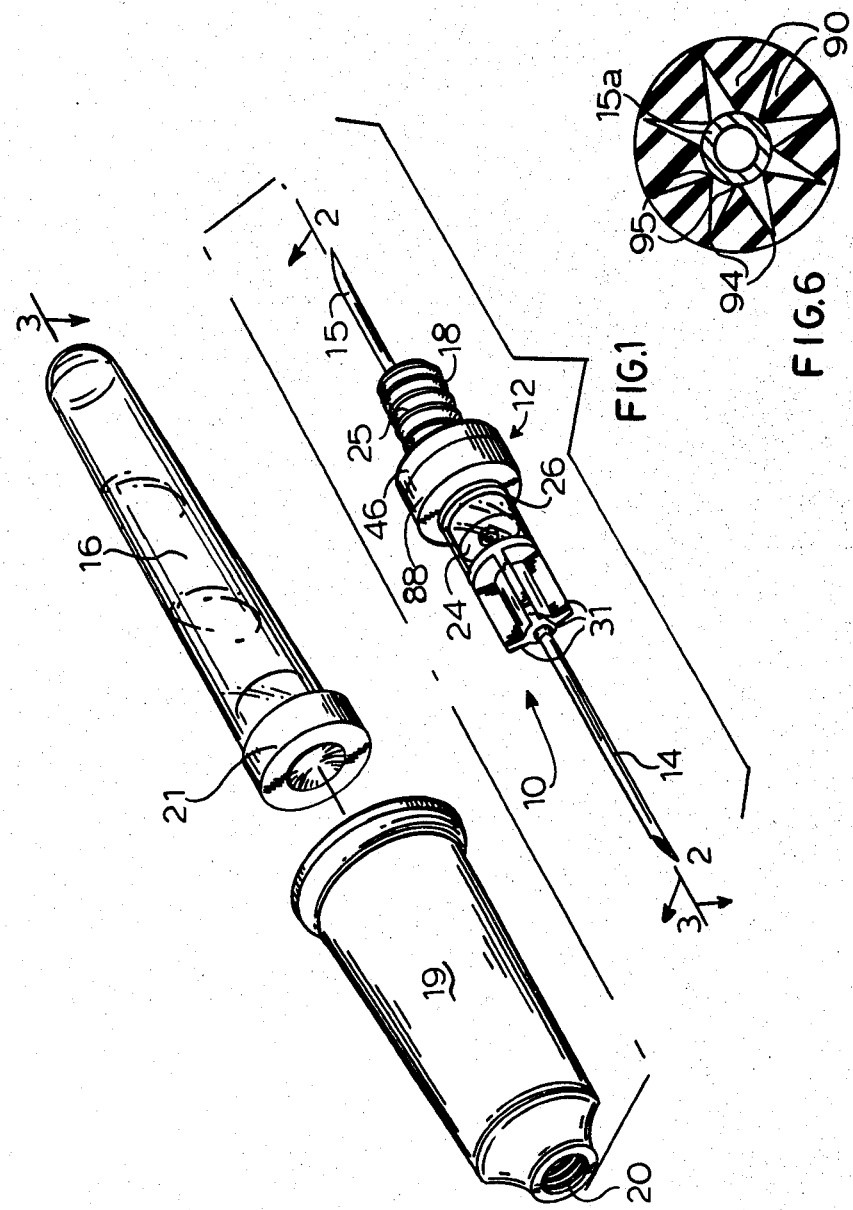
FIG. 1 is an exploded perspective view of a sample collection needle assembly, a holder for an evacuated container, and an evacuated blood collection container for use in obtaining blood samples from a patient.

Referring to the drawings in which like reference characters refer to like parts throughout the several views thereof, FIG. 1 shows the basic external components of needle assembly 10, including a housing 12, a first needle cannula 14 adapted for insertion into a patient and a second negative pressure needle cannula 15 at the opposite end of housing 12. The second needle cannula is adapted for penetration into an evacuated container 16 for collection of a blood sample. Housing 12 includes a portion 25 having threads 18 adjacent second cannula 15 onto which a container holder 19 is threaded by its internal mating threads 20 at the forward end of the holder. Evacuated container 16 is inserted into holder 19 so that second needle cannula 15 penetrates the stopper 21 at the forward end of the evacuated container 16. These general aspects of sample blood collection assemblies are well known to those skilled in the art.

Figure 2:
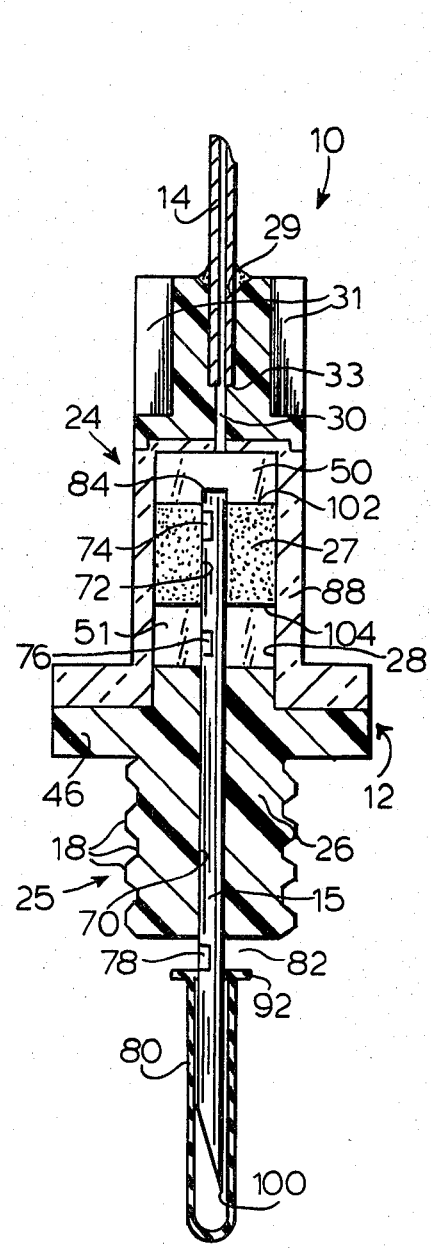
FIG. 2 is an enlarged cross-sectional view taken along lines 2—2 of FIG. 1 and illustrating one embodiment of the invention.

Referring to FIG. 2, housing 12 has a forward end 24 and a rearward end 25, with these ends being, preferably, separable in order to insert porous plug 27. Forward end 24 is, preferably, cylindrical and has a large bore 28 therein for receiving in reciprocal manner porous plug 27 therein. At the other end of this section, a smaller bore 29 is arranged to receive needle cannula 14 therein. In this embodiment, smaller bore 29 extends to a still smaller diameter channel 30 which interconnects bore 29 with bore 28. At the junction between bore 29 and channel 30, a shoulder 33 is formed for receiving cannula 14 in an abutting relationship. Cannula 14 may be held in bore 29 by a suitable adhesive. It will be appreciated by practitioners-in-the-art that channel 30 is not essential to the structure here, but is merely a preferred arrangement. Moreover, the diameter of channel 30 may be varied to provide a regulation of the fluid flow rate therethrough.

Forward end 24 of the housing also includes a number of longitudinal ribs 31 surrounding the outwardly extending cannula. A needle shield (not shown) generally covers the outwardly extending needle cannula and includes mating internal ribs within. The mating ribs between the needle shield and the needle assembly allow the user to facilitate the insertion into or removal of the needle assembly from the tube holder. Forward end 24 also includes an annular flange 32 which serves to provide a surface for joining the two portions of the housing together upon assembly. Once again, suitable fastening means, such as adhesives or the like, may be used to secure the two portions of the housing together.

Rearward end 25 includes a short protruding cylindrical portion 40, sized to fit within bore 28 of the forward end. At the opposite side of this rearward end, external threads 18 are provided on portion 26 of rearward end 25, as previously mentioned as a connection mechanism to the tube holder. A bore 70 extends through rearward end 25 of the housing, which is similar to bore 29 in the forward end of the housing. Once again, bore 70 is sized to accept the diameter of a second needle cannula 15, which is secured to bore 70 by appropriate means such as adhesives, for example. An annular flange 46 is arranged to cooperate with flange 32 in joining the ends 24, 25 of the housing togehter. It will be appreciated, that upon assembling the two portions of the housing together, with the valve 27 positioned therein, flanges 32 and 46 may be secured together by appropriate fastening means such as adhesives, for example. The bore 28 of forward end 24 defines a tubular chamber 50 for receiving the liquid sample of interest.

In order to observe the contents of chamber 50, and to provide an indication to the user of the device that access to a vein has been obtained, the annular wall 88 of the forward end which defines chamber 50 is, preferably, comprised of a translucent or transparent material. For manufacturing purposes, it is preferable to make the entire forward end of the needle assembly from a translucent material such as a rigid thermoplastic, as will be appreciated by practitioners-in-the-art. However, various sealed windows, ports or other means for a user to view the contents of chamber 50 are within the purview of this invention.

Porous plug 27, is mounted for reciprocation in bore 28, and includes an internal bore 72 for receiving in reciprocal engagement the front end of negative pressure cannula 15. Porous plug 27, is cylindrical in shape, as will be appreciated, to conform to bore 28 and is of a size to engage the walls of chamber 50 in liquid sealing engagement but still of the size to allow reciprocation of plug 27 in bore 28 under the action of a pressure differential on opposite surfaces thereof.

Porous plug 27 is a gas permeable, liquid impermeable material arranged to allow the passage of a gas therethrough such as air, for example, but not liquid such as blood, for example. As purely illustrative of materials which may be used to form porous plug 27, one may select polyethylene, such as sintered polyethylene, or an open cell polyethylene foam, or other similar moldable polymeric materials, such as porous polypropylene, or porous polyfluorocarbons.

As can be seen in FIG. 2, a negative pressure cannula 15 includes a notch 74 adjacent the end 84 of the cannula 15. The end 84, in this connection, is plugged or crimped or otherwise closed off while notch 74 provides communication between chamber 50 and the lumen of cannula 15, depending upon the positioning of porous plug 27. An additional notch or opening 76 is also provided in cannula 15 to provide flow communication between the rear end 51 of chamber 50 and the lumen of cannula 15. As can be seen further in FIG. 2, a third notch or opening 78 is provided which allows flow communication between the atmosphere or the external area around the assembly of the invention and the lumen of cannula 15.

Figure 5:
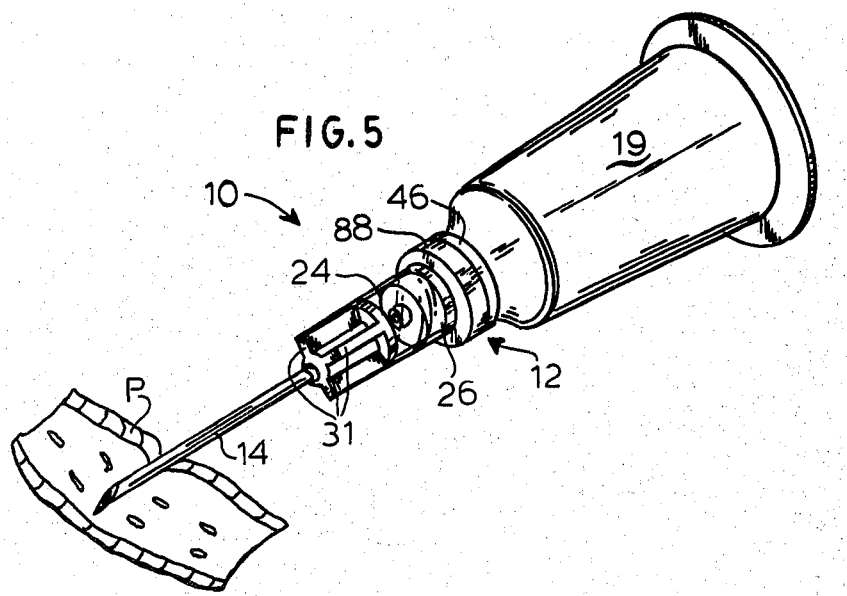
FIG. 5 is a perspective view of a needle assembly connected to a holder inserted into a patient so that a user can view the assembly for indication of vein entry.

Referring now to FIG. 5, the needle assembly 10 is illustrated connected to a sample holder 19. Cannula 14 is shown inserted into a patient P during the venipuncture. When I.V. cannula 14 enters the vein of patient P, blood flows from the vein through cannula 14 and reduced diameter passage 30 into chamber 50. As the blood enters chamber 50, air therein is displaced from chamber 50 through porous plug 27. However, because of the character of porous plug 27, the blood does not pass therethrough. Air passing through plug 27 is displaced from the chamber 50, through notches 74, 76 and then through the lumen of cannula 15 and out notch 78 in the area 82 (FIG. 2) between the flange 92 of flexible sleeve 80 covering the outer end of negative pressure cannula 15, and end surface 106 of housing end 25. At this point, plug 27 remains positioned as shown in FIG. 2 with the notch or orifice 74 covered. At this point, further, a sample of the blood from patient P is positioned in chamber 50.

Figure 3:
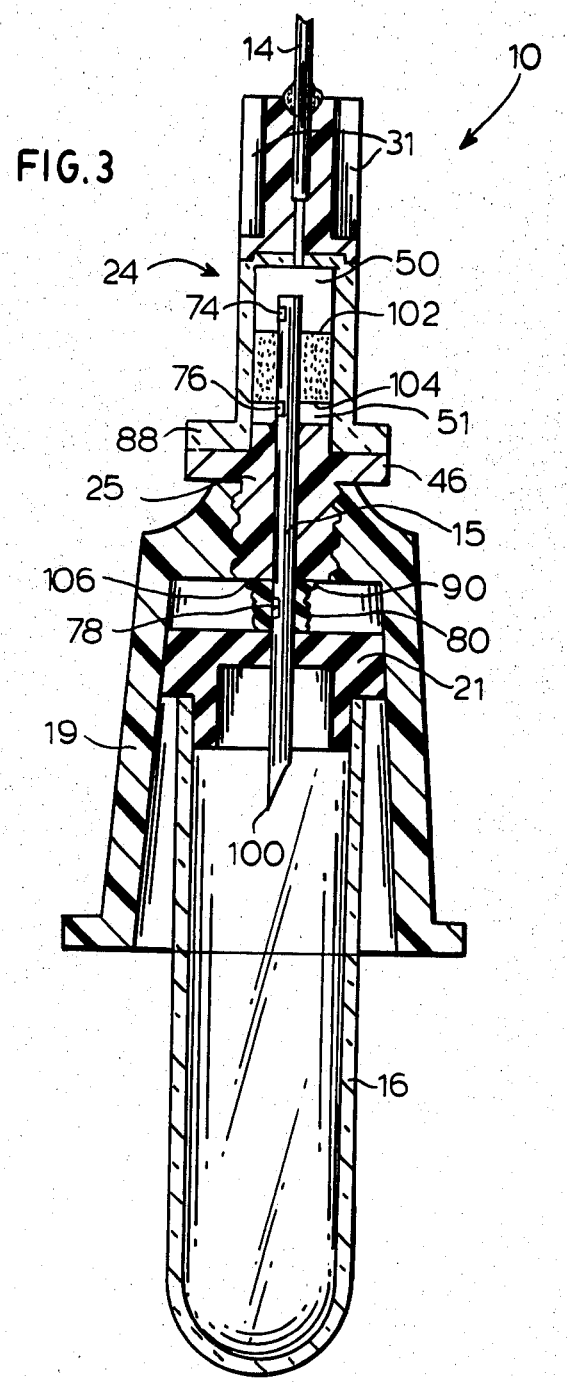
FIG. 3 is an enlarged cross-sectional view taken along lines 3—3 of FIG. 1.

Referring now to FIG. 3, it will be seen that the assembly includes the holder 19 mounted on the hub portion 26 of the rearward housing 25. An evacuated blood collection container 16 is shown engaged in holder 19 with the resilient plug 21 thereof penetrated by the end or point 100 of negative pressure cannula 15. Because of the vacuum set up once cannula 15 penetrates stopper 21, this vacuum or negative pressure draws any air left in chamber 50 through porous plug 27 by communication between the internal area of evacuated container 16 through the lumen of cannula 15 and notches 74, 76. Because plug 27 is more occluded with blood, a pressure differential is built up between the upper chamber 50 and the lower chamber 51, the plug moves downwardly toward the face of extension 40 as shown in FIG. 3.

This movement causes plug 27 to uncover notch or opening 74. Any residual air blocked in portion 51 passes through notch 76 during this movement to enhance the movement of plug 27, downwardly. When notch 74 is uncovered, a flow communication is provided between chamber 50 and the evacuated container 16, through the lumen of negative pressure cannula 15. In the meantime, upon insertion of the container 16 into holder 19 and the penetration of the stopper thereof by the point 100 of cannula 15, the flexible sleeve 80 is moved upwardly to the position as shown in FIG. 3 wherein the upper flange 92 thereof engages the bottom surface 106 of extension 26. Thus, the sample previously withdrawn from the vein of patient P which was drawn into chamber 50, moves into the evacuated collection container 16. Once the sample is withdrawn into container 16, container 16 is removed from holder 19, thus causing the flexible sleeve 80 to move back to a position where it still blocks notch 78 and covers the end 100 of negative pressure cannula 15, thus allowing the I.V. needle 14 to remain in the vein without leakage for rendering the assembly available for the sequential placement of containers 16 in holder 19 for receiving multiple samples of blood.

Figure 4:
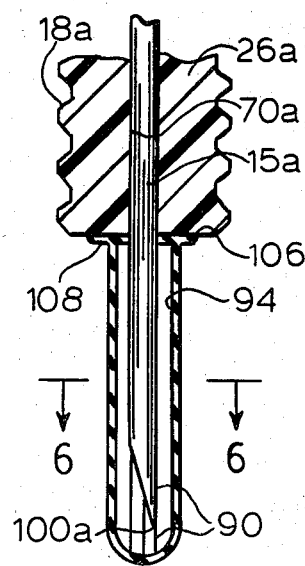
FIG. 4 is a partial sectional view similar to the view of FIG. 2, but illustrating a further embodiment of the invention.

Referring now to FIG. 4, an alternative embodiment is shown wherein notch 78 is not used in negative pressure cannula 15a. In this arrangement, like parts are numbered with the same reference numbers and the additional reference a. In this embodiment, as a substitute for the air passage or opening 78 in cannula 15a, a sleeve 90 is configured so as to be positioned always with its flange 108 adjacent and in close but gas non-sealing engagement with the surface 106a of extension 26a. As can be seen in FIG. 6, sleeve 90 is arranged for sliding engagement on cannula 15a. However, it includes a plurality of internal grooves 94 with the inner points 95 of the grooves actually engaging the outer surfaces of cannula 15a. The grooves, therefore, provide gas communication between cannula end 100a and the upper end of sleeve 90 where the air leaks out between the adjacent surfaces of flange 108 of sleeve 90 and surface 106a of extension 26a. The grooves 94 are of a size to allow passage of gas, but prevent passage of liquid. It will be appreciated that the upper surface of flange 108 may contain grooves, also, for providing a venting action between end 100a and the atmosphere.

Figure 7:
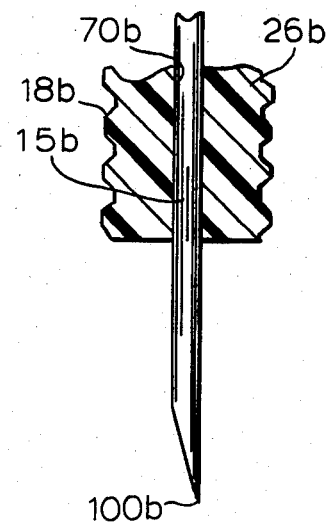
FIG. 7 is an enlarged partial cross-sectional view similar to FIG. 2 but illustrating a further embodiment of the invention illustrating a single sample needle collection assembly.

As further illustrative of the invention herein, wherein a single sample blood collecting assembly is provided, one may note the assembly shown in FIG. 7. As can be seen in that assembly, no specific sleeve 80 is utilized and cannula 15b does not include a third notch or opening as notch 78 in the embodiment shown in FIG. 2. Thus, when I.V. cannula 14 is inserted into the vein of a patient, liquid flow communication is provided between the vein and the chamber 50, and a sample is collected in the chamber 50. The arrangement is such, as in the embodiment shown in FIG. 2, that the sample does not flow through porous plug 27. However, air displaced by the blood sample entering chamber 50 passes through the air permeable plug 27 and through notches 74, 76, the lumen of cannula 15, and out the end 100b of negative pressure cannula 15b. Then, when a holder is mounted on extension 26b and the point 100b of cannula 15b is inserted through a plug into an evacuated blood collection container 16, the same pressure differential is provided between the upper chamber 50 and the lower chamber 51 from plug 27, so that the plug moves downwardly, opening notch 74. This provides liquid flow communication between chamber 50 and the evacuated container 16 for collection of the single sample into the evacuated container 16. In this embodiment, since no further sample is being collected by the assembly, the I.V. cannula 14 has already been removed from the vein of the patient P, and the assembly is discarded since the single desired sample has been collected into the evacuated container.

Figure 8A:
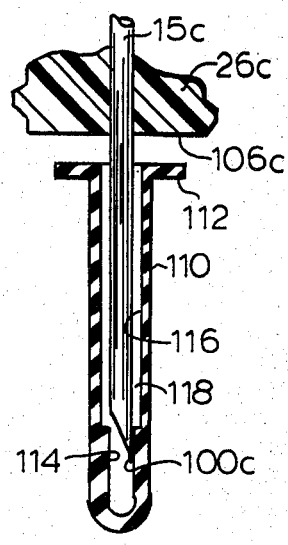
FIG. 8a is an enlarged partial cross-sectional view of still another embodiment illustrating the invention utilizing a cooperating flexible sleeve with a stepped internal diameter in a venting position.
Figure 8B:
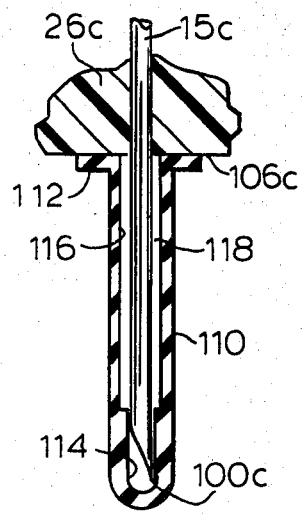
FIG. 8b is the embodiment of FIG. 8a in a closed non-venting position.

A further multiple sample collection embodiment is shown in FIGS. 8a and 8b similar to the embodiment shown in FIG. 4, for allowing air bleeding between point 100c of negative pressure cannula 15c and the atmosphere. In this embodiment, the internal diameter of sleeve 110 is stepped to provide a smaller internal bore 114 in sleeve 110, which is of a diameter which seals with the outer surface of cannula 15c, and a larger internal bore 116, which allows a venting passage 118 between the cooperating surfaces of sleeve 110 and cannula 15. Thus, in the position shown in FIG. 8a, venting may take place between end 100c of cannula 15c and the atmosphere through passage 118, while in the position shown in FIG. 8b, passage 118 is closed, preventing any venting.

Thus, as will be appreciated from the above discussion, a blood collecting needle assembly is provided in accordance with this invention for collecting either single or multiple samples, as required, in combination with an arrangement for indicating vein entry to the user of the assembly. Moreover, the arrangement of invention here in the form of a simplified porous plug operating to provide, simultaneously, passage of a gas and blockage of a liquid, and to function as a valve is an extremely simplified and inexpensive arrangement of apparatus for manufacture. It is particularly appropriate for mass production techniques, as will be understood by practitioners-in-the-art.

While the methods and forms of apparatus herein described constitute preferred embodiments of the invention, it is to be understood that the invention is not limited to these precise methods and forms of apparatus, and that changes may be made therein without departing from the scope of the invention which is defined in the appended claims.

What is claimed is:

1. A needle assembly for collecting one or more liquid samples from a source for subsequent discharge into evacuated containers, comprising
   (a) a housing having a forward end and a rearward end;
   (b) a sample collection chamber in said housing;
   (c) a first access opening in said forward end in liquid flow communication with said chamber;
   (d) a first cannula extending outwardly from said first access opening for insertion into said source;
   (e) a second access opening in said rearward end in flow communication with said chamber; the improvement characterized by
   (f) a second cannula positioned in said second access opening and extending into said chamber to a point spaced from said first access opening;
   (g) said second cannula having a first and a second spaced apart opening therein in the part thereof extending into said chamber, said spaced apart openings providing flow communication between said chamber and the lumen of said second cannula; and
   (h) a gas permeable, liquid impermeable annular porous plug positioned for reciprocation in said chamber along said second cannula from a first position in which said first opening is covered by said porous plug and said second opening is uncovered, to a second position in which said first opening is uncovered;
   (i) whereby when said first cannula engages said source, liquid enters said chamber by forcing any gas therein through said porous plug, and out said second cannula through said first and second openings, and when said second cannula comes into contact with an evacuated container, said porous plug moves toward said second access opening under the influence of a pressure differential on either side thereof, uncovering said first opening and forcing residual air out said second opening on the side of said plug facing said rearward end, to that liquid in said chamber passes through said second cannula to said evacuated container.

2. The apparatus of claim 1, further characterized by
   (a) said porous plug is comprised of a member selected from the group consisting of sintered polyethylene, open cell polyethylene foam; porous polypropylene, porous polyfluorocarbons, and mixtures thereof.

3. The apparatus of claim 1, further characterized by
   (a) a third opening in said second cannula in the part thereof extending out of said housing;
   (b) a resilient sleeve extending over the end of said second cannula extending out of said housing and opposite said chamber; and
   (c) said sleeve adapted to cover said third opening when an evacuated container is penetrated by said second cannula.

4. The apparatus of claim 3, further characterized by
   (a) said housing including means for connecting a holder for an evacuated container.

5. The apparatus of claim 1, further characterized by
   (a) a resilient sleeve slidingly engaging the said second cannula on the end thereof extending out of said housing and opposite said chamber;
   (b) an internal cannula engaging surface on said sleeve comprised of a plurality of longitudinally extending grooves; and
   (c) said grooves in engagement with said cannula being gas permeable and liquid impermeable.

6. The apparatus of claim 1, further characterized by
   (a) said housing including means for connecting a holder for an evacuated container.

7. The apparatus of claim 6, further characterized by
   (a) a holder for an evacuated container connected to said housing.

8. The apparatus of claim 1, further characterized by
   (a) said housing including means for viewing the contents of said chamber.

9. The apparatus of claim 8, further characterized by
   (a) said viewing means is translucent housing walls adjacent said chamber.

10. The apparatus of claim 1, further characterized by
    (a) a resilient sleeve slidingly engaging the said second cannula along the external surface thereof at the end of said second cannula extending out of said housing and opposite said chamber;
    (b) a longitudinally extending internal cannula engaging surface on said sleeve comprised of a stepped internal surface;
    (c) one portion of said longitudinal extent of said stepped internal surface defining a smaller internal bore of a diameter to sealingly engage with the cooperating external surface of said second cannula; and
    (d) another portion of said longitudinal extent of said stepped internal surface defining a larger internal bore of a diameter to define an air passage with the cooperating external surface of said second cannula.

* * * * *